United States Patent [19]

Kaplan

[11] Patent Number: 5,955,112
[45] Date of Patent: Sep. 21, 1999

[54] NON-STINGING STYPTIC PENCIL

[76] Inventor: Jeffrey Kaplan, P.O. Box 11106, Ft. Laud, Fla. 33339

[21] Appl. No.: 09/044,219

[22] Filed: Feb. 11, 1998

[51] Int. Cl.$^6$ .............................. A61K 33/06; A61K 7/48; A61K 9/00; A61M 35/00

[52] U.S. Cl. ................... 424/682; 424/698; 424/DIG. 5; 424/195.1; 424/401; 514/626; 514/772.1; 514/772.3; 514/772.4; 514/828; 514/953; 604/309

[58] Field of Search .................. 424/682, 698, 424/DIG. 5, 195.1, 401; 514/626, 772.1, 772.3, 772.4, 828, 953; 604/309

[56] References Cited

U.S. PATENT DOCUMENTS

| | | | |
|---|---|---|---|
| 459,738 | 9/1891 | Black | 424/646 |
| 497,659 | 5/1893 | Harned | 424/401 |
| 819,901 | 5/1906 | Maschal | 424/401 |
| 3,113,568 | 12/1963 | Robins | 126/186 |
| 3,506,009 | 4/1970 | Di Pietro | 264/279 |
| 4,022,203 | 5/1977 | Ackley | 128/156 |
| 4,166,108 | 8/1979 | Brown et al. | 424/28 |
| 4,233,976 | 11/1980 | Dunshee | 128/260 |
| 5,279,837 | 1/1994 | Hill | 424/682 |
| 5,785,955 | 7/1998 | Fischer | 424/49 |

OTHER PUBLICATIONS

Remington's Pharmaceutical Sciences, 18th ed., Mack Printing Co., Easton (PA), 1990, p. 761.
The Chemical Formulary, The Chemical Formulary Co., NY, 1933, vol. 1, pp. 132–133.
The Chemical Formulary, The Chemical Formulary Co., NY, 1936, vol. 2, p. 141.
The Chemical Formulary, The Chemical Publishing Co. of New York, Inc., NY, 1939, vol. 4, p. 86.
The Chemical Formulary, Chemical Publishing Co., Inc., NY, 1957, vol. 10, p. 81.
The Chemical Formulary, Chemical Publishing Co., Inc., NY, 1961, vol. 11, p. 118.

*Primary Examiner*—John Pak

[57] ABSTRACT

A non-stinging styptic composition in the form of a water soluble resin coated cast pencil, for stopping bleeding from cuts and nicks received during shaving. The composition comprises aluminum sulfate, aloe, glycerine, lidocaine and polyethylene glycol 400.

3 Claims, No Drawings

NON-STINGING STYPTIC PENCIL

BACKGROUND

1. Field Of Invention

This invention relates to an improved styptic pencil composition for use primarily in connection with shaving to rapidly and effectively curtail bleeding from minor nicks and cuts, which when applied does not sting, irritate or cause staining on clothing.

2. Discussion Of Prior Art

Nicks and cuts on the chin, face and other areas are a virtually inevitable consequence of regular blade shaving. Nicks and cuts can also be a significant problem for woman when shaving their legs and underarms. Shaving cuts, especially in the area of the face tend to bleed profusely, and it can be quite difficult to halt the flow of blood.

The use of styptic or astringent compositions is well established in the art. The principal astringent chemicals are compounds of aluminum, zinc, manganese, iron, and bismuth, and other chemical groups that contain these metals (such as permanganates).

Although some astringent substances are potent chemicals, they do not enter human body cells-which is their virtue. Rather, all their activity occurs at the cell surface-where they block noxious substances from entering the cell or the space between cells. They coagulate body chemicals so that they form clots, crusts, or other solid deposits.

To go back to the original example of the man who cuts himself while shaving, an astringent styptic pencil is normally used. These styptic pencils have been in use since 1890 and usually consist of 90% aluminum sulfate and 10% of an inert filler.

Typical styptic compositions in stick and pencil forms are set forth in the U.S. Pat. No. 819,901 to Maschal (1906), in U.S. Pat. No. 459,738 to Black (1890) and in U.S. Pat. No. 497,659 to Harned (1892).

These examples are comprised of aluminum sulfate which has been dried and either placed on a stick or formed into a pencil. Unfortunately, the acidic nature of the salts also cause a stinging sensation which often exceeds the pain caused by the original wound and can also result in scarring or redness of the area where the stick is applied.

Furthermore, the stick must be wetted before each, and when the stick is stored between uses, the stick can harden, stick to its container, and become difficult to rewet and reuse.

A third drawback of some of the highly acidic compositions is its deleterious effect on any clothing with which it may come into contact. According to the type of composition and fabric, the clothing could be endelibly stained or even deteriorated.

In various attempts to obviate these problems, several different styptic devices have been introduced. These consists of various styptic bandages as described in U.S. Pat. No. 3,113,568 to Robins (1963), in U.S. Pat. No. 4,022,203 to Ackley (1977), in U.S. Pat. No. 4,233,976 to Dunshee (1980).

Unfortunately these styptic devices have many disadvantages. In U.S. Pat. No's 3,113,568, and U.S. Pat. No. 4,022,203, the composition used is again, aluminum sulfate or a comparable metal salt astringent which still causes a stinging sensation when applied to the wound. Another major problem is the fact that when the bandage is removed the clot which has adhered to the absorbant pad is also removed and bleeding occurs again.

In U.S. Pat. No. 4,233,976, this clot problem is addressed by the introduction of a thin, highly porous translucent cloth like fabric which is saturated with aluminum sulfate. This finger-tearable material has the disadvantage of falling apart when applied to the wet skin. Its toilet paper consistency sticks to ones fingers and is impractible to use. In addition, the 0.9 grams of aluminum sulfate per cubic centimeter which is applied to the fabric isn't substantial enough to stop the flow of blood from the wound.

Two other attempts to obviate the current styptic problems mentioned are described in U.S. Pat. No. 4,166,108 to Brown (1979) and in U.S. Pat. No. 5,279,837 to Hill (1994).

The above mentioned prior art are primarily cream compositions which has many disadvantages. In U.S. Pat. No. 4,166,108, this cream composition is designed to be applied to major, open wounds without fear of shock. The disclosed composition contain 25% or less by weight of the metal salt. The disclosed composition would not be completely satisfactory for application to shaving cuts. Due to the small amount of metal salt, the composition would not act to halt bleeding from a small cut substantially immediately, and would have to be reapplied repeatedly.

In U.S. Pat. No. 5,279,837, a cream composition is also disclosed. Unfortunately, the use of a cream which tends to harden after application is difficult to wash off and is undesirable.

Thus, a need exists for a fast acting non-stinging, non-staining styptic composition in the form of the familiar cast pencil shape, which substantially immediately curtails bleeding from a small cut upon application, yet avoids the disadvantages associated with the mentioned prior art.

OBJECTS AND ADVANTAGES

Accordingly, several objects and advantages of my invention are:

(a) to provide a novel styptic composition which overcomes or substantially alleviates the problems of the prior art.

(b) to provide a novel styptic composition which does not sting when applied to a wound.

(c) to provide a novel styptic composition which does not stain ones clothing.

(d) to provide a novel styptic composition in the form of a cast pencil which is stable and does not dry out resulting in a crumbling, unsightly powder.

(e) to provide a novel styptic composition in the form of a cast pencil carried by water soluble low melting point resin.

(f) to provide a novel styptic composition which can be impregnated into the pad of prepackaged bandages and does not cause stinging or staining.

(g) to provide a novel styptic composition that is low cost, neat appearing, versatile and reliable product.

DETAILED DESCRIPTION OF THE INVENTION

In the present invention, the foregoing difficulties are obviated in that there is provided a non-stinging, non-staining styptic composition carried by a water dispersible low melting point resinous material in a dry form. In a preferred embodiment, the composition is in the form of a cast pencil.

In accordance with the invention, the composition is formulated by initially forming a liquid mixture containing the astringent and anethestic ingredients. This is achieved by liquifying aluminum sulfate by aid of heat. Remove any scum and avoid overheating. The molten liquid should be clear. If a white color is desired, triturate and add in a mixture of french powder or equivalent whitening ingredient. Add glycerine, aloe and lidocaine to the liquid alum and pour into suitable molds. After solidifying by cooling, remove the pencils and dip into a liquified solution of polyethylene glycol 400. Remove and let solidify by cooling.

Another variation of the invention is acheived by liquifying aluminum sulfate by aid of heat. Remove any scum and avoid overheating. Add glycerine, aloe, lidocaine and dissolved polyethylene glycol 400. Pour into suitable molds. After solidifying by cooling, remove and package.

Accordingly, the reader will see that the styptic composition is dispersed in the melted resin, either as a true solution therein, or as a colloidal solution, or as a suspension, depending on the nature and concentration of the composition and the nature of the resin.

The resulting resin-coated styptic pencils can be utilized by wetting. Water will cause the resin to soften and partially dissolve. The styptic composition is then applied to the zone requiring the composition.

This invention is not restricted to the use of any particular water dispersible low melting resinous material. Of course it is necessary to use a water soluble low melting point resin which is non-toxic and a non-irritant. A suitable resin is polyethylene glycol. The polyethylene glycols are available in the variety of grades, are waxy in appearance and texture and have a relatively low melting point. Polyethylene glycol 400 melts at about 25° C., while Polyethylene glycol 4000 has a melting point of approximately 55° C. Polyethylene glycol 400, which is considerably softer than Polyethylene 4000, improves the smoothness and uniformity of the resulting coating. Other suitable water dispersible, low melting point resins which could be used in accordance with the invention are the polyoxyalkylene derivatives of lanolins and lanolin alcohols, polyoxyalkylene derivatives of sorbitol and lanolin, polyoxy-ethylene sorbitan tristearate, polyoxyethylene lauryl ether and polyoxyethylene derivatives of sorbitol and beeswax.

Polyethylene glycol is the preferred water soluble resinous carrier not only because of its low melting point but also because of its waxy nature which enables it to act as a lubricant when applied.

The following example is given as specific illustration of the invention. It should be understood, however, that the invention is not limited to the specific details set forth therein. In the following example all percentages are by weight of the total composition:

EXAMPLE 1

| COMPONENT | PERCENT (w/w) |
|---|---|
| Aluminum Sulfate | 80 |
| Aloe Vera | 5 |
| Glycerine | 5 |
| Lidocaine | 5 |
| Polyethylene glycol 400 | 15 |

The formula-was prepared by liquifying the aluminum sulfate with heat. The remaining constituents were added serially and mixed thoroughly. The formulation was poured into suitable molds and cooled to solidify.

CONCLUSION, RAMIFICATION AND SCOPE OF THE INVENTION

Accordingly, the reader will see that a non-stinging, non-staining composition of the inventor provides that:

it permits a comfortable remedy to the curtailing of bleeding from small nicks and cuts received from blade shaving.

it provides a non-staining composition to ones clothing.

it provides a solution to the brittle, drying and sticking properties associated with current styptic pencils available to the public.

Those skilled in the art will have no difficulty in determining suitable proportions of the above agents to be used. The invention has been described as applied to preferred embodiments and it will be understood that various substitutions and changes may be effected without departing from the spirit and scope of the novel concepts and principals of this invention.

I claim:

1. A styptic pencil for application to minor shaving cuts comprising a molded cast styptic pencil comprising aluminum sulfate in a styptic-effective amount, glycerine, aloe, lidocaine, and water soluble, low melting point polyethylene glycol that has a melting point of between about 25° C. to about 55° C., wherein the polyethylene glycol is present and in an amount up to about 15 percent by weight.

2. A method of preparing the styptic pencil of claim 1 comprising the steps of:

a) heating a styptic-effective amount of aluminum sulfate;

b) adding glycerine, aloe and lidocaine to the heated aluminum sulfate to formulate a uniform liquid mixture;

c) solidifying the uniform liquid mixture by cooling into a solid material formed in a molded pencil shaped cast;

d) melting a water soluble, low melting point polyethylene glycol that has a melting point of between about 25° C. to about 55° C., wherein the polyethylene glycol is present and in an amount up to about 15 percent by weight of the total weight of aluminum sulfate, glycerine, aloe, lidocaine and the polyethylene glycol;

e) applying the melted polyethylene glycol to said solid material formed in a molded pencil shaped cast; and f) cooling to re-solidify.

3. A method of preparing the styptic pencil of claim 1 comprising the steps of:

a) heating a styptic-effective amount of aluminum sulfate;

b) adding glycerine, aloe, lidocaine and melted water soluble, low melting point polyethylene glycol that has a melting point of between about 25° C. to about 55° C., wherein the polyethylene glycol is present and in an amount up to about 15 percent by weight of the total weight of aluminum sulfate, glycerine, aloe, lidocaine and the polyethylene glycol, to formulate a uniform liquid mixture; and c) solidifying the uniform liquid mixture by cooling into a solid material formed in a molded pencil shaped cast.

* * * * *